(12) United States Patent
Larson, III et al.

(10) Patent No.: US 6,491,671 B1
(45) Date of Patent: Dec. 10, 2002

(54) MICROCATHETER WITH HEMODYNAMIC GUIDE STRUCTURE

(75) Inventors: Theodore C. Larson, III, Nashville, TN (US); Mark K. McQuain, Nashville, TN (US); Robert J. Roselli, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 24 days.

(21) Appl. No.: 09/805,861

(22) Filed: Mar. 14, 2001

Related U.S. Application Data

(60) Provisional application No. 60/189,242, filed on Mar. 14, 2000, and provisional application No. 60/189,719, filed on Mar. 15, 2000.

(51) Int. Cl.⁷ .............................................. A61M 25/01
(52) U.S. Cl. ........................ 604/264; 604/528; 604/510; 604/508
(58) Field of Search ................................ 604/264, 270, 604/528, 523, 95.01, 93.01, 164.13, 500, 507, 508, 510; 600/434, 585

(56) References Cited

U.S. PATENT DOCUMENTS

| 4,671,295 | A | * | 6/1987 | Abrams et al. ............. 600/463 |
| 4,722,347 | A | * | 2/1988 | Abrams et al. ............. 600/437 |
| 5,336,205 | A | | 8/1994 | Zenzen et al. ............. 604/280 |
| 5,601,538 | A | | 2/1997 | Deem ........................ 604/280 |
| 5,722,415 | A | * | 3/1998 | Rom et al. ................. 600/374 |
| 5,833,624 | A | * | 11/1998 | Rom et al. ................. 600/454 |
| 5,899,890 | A | | 5/1999 | Chiang et al. ............. 604/264 |
| 5,928,260 | A | * | 7/1999 | Chin et al. ................. 604/107 |

OTHER PUBLICATIONS

Benati, Et Al.; Preoperative Embolization of Arteriovenous Malformations with Polylene Threads: Technigues with Wing microcatheter and Pathologic Results; AJNR:10; May/Jun. 1989; pp. 579–586.

* cited by examiner

*Primary Examiner*—Patrick Brinson
(74) *Attorney, Agent, or Firm*—Waddey & Patterson; Mark J. Patterson

(57) ABSTRACT

A catheter device for therapeutic and diagnostic use within a human vascular system has a catheter body with a hub located at a proximal end of the catheter body, and a tip located at a distal end of the body. A guide structure is connected to the catheter body proximate the tip, with the guide structure having a wing shape that provides hemodynamic lift in response to laminar blood flow around the catheter. The wing shape of the guide structure tapers down from a leading edge to a trailing edge, with the leading edge facing the catheter tip so that when the catheter is positioned inside a vessel wall of the vascular system and oriented in a downstream direction, the lift created by the laminar blood flow biases the catheter tip toward the vessel wall. Preferably, the distal end of the catheter body comprises a flexible material so that the catheter tip can deflect laterally towards the vessel wall in response to the hemodynamic lift. An intermediate section of the catheter body between the hub and the tip provides a semi-rigid control connection whereby pushing, pulling, and rotation of the hub produces a corresponding movement of the catheter tip.

9 Claims, 4 Drawing Sheets

MICROCATHETER WITH HEMODYNAMIC GUIDE STRUCTURE

This application claims benefit of co-pending U.S. Provisional Patent Application Serial No. 60/189,242 filed Mar. 14, 2000, entitled "Winged Microcatheter" and U.S. Provisional Patent Application Serial No. 60/189,719 filed Mar. 15, 2000, entitled "Winged Microcatheter."

A portion of the disclosure of this patent document contains material which is subject to copyright protection. The copyright owner has no objection to the facsimile reproduction by anyone of the patent document or the patent disclosure, as it appears in the U.S. Patent and Trademark office patent file or records, but otherwise reserves all copyright rights whatsoever.

BACKGROUND OF THE INVENTION

The present invention concerns the use of catheters in the field of interventional neuroradiology. In particular, this invention pertains to microcatheters provided with auxiliary guide structures to permit safe navigation of the catheter within the intracranial vessels for embolization of high flow vascular lesions.

Microcatheter technology has advanced from the 1980's to the point that a microcatheter is now commonly used in the treatment of vascular lesions of the central nervous system. Microcatheters are low profile catheters used to treat strokes, cerebral aneurysms, fistulas, arterial venous malformations, and other areas by occluding the pathologic vascular abnormality through an endovascular approach utilizing selective deposition of coils, particles, balloons, or liquid adhesives. Such microcatheters can also be used in other areas of the body.

In these delicate procedures, a major difficulty involves steering the catheter through the tortuous bifurcations of the cerebral arteries to navigate it to the site of treatment. Catheter steering difficulties often add hours of time and complications to the procedure making it impractical to treat some areas of the brain. The ability to steer the catheter precisely and quickly is essential for effective catheterizations with minimal risks.

Endovascular treatment of cerebral vascular lesions employs one of two classes of microcatheter, either a flow directed microcatheter or a guidewire directed microcatheter. Flow directed microcatheters typically have a curve steamed in the tip of the microcatheter and are advanced through the vessel based on the amount of blood flow, assisted by externally advancing the catheter, sometimes from a small guidewire. In some cerebral vascular pathologies, a flow directed microcatheter is unable to reach its target, particularly in those areas with slower flow. A guidewire directed microcatheter, on the other hand, is advanced based on catheterization using a micro-guidewire and pushing the catheter distally. This increases the risk of vessel perforation by the guidewire and is often limited by an inability to push the catheter around numerous turns.

As used in the prior art, a guide catheter is first advanced from the femoral artery by a percutaneous method, terminating in a carotid or vertebral artery. A microcatheter is then advanced through the guide catheter into the cervical and cerebral vasculature. The placement of such a microcatheter is accomplished either by use of a guidewire or by taking advantage of hemodynamics. Each of these conventional methodologies has drawbacks. The guidewire directed microcatheter risks puncturing a vessel or aneurysm with significant hemorrhagic consequences intracranially. The flow directed microcatheter frequently lacks control directionality. New guidewires may now be used with flow directed microcatheters, however, this reintroduces the risks associated with the use of a guidewire and also raises the possibility of puncturing the wall of the flow directed soft microcatheter. Delivery of the greatest variety of embolic agents is usually possible only through a guidewire directed catheter. A more limited selection of embolization materials can be delivered through a flow directed microcatheter due to its suppleness.

What is needed, then, is a microcatheter than can be quickly and precisely guided through the vascular system for treatment of cerebral vascular lesions, with a reduced risk of vessel perforation.

SUMMARY OF THE INVENTION

The microcatheter of the present invention combines a catheter body with a hemodynamic guide structure attached to the catheter body proximal to its distal orifice. The guide structure is wing-shaped to take advantage of Bernoulli's principal and the kinetic energy of laminar blood flow around the catheter. The wing provides hemodynamic lift to move the catheter tip toward vessel walls and into a vessel bifurcation branch.

The wing-shaped guide structure generates lift from hemodynamic flow similar to that commonly employed by wings on conventional aircraft. This lift can be used to direct the tip of the microcatheter into a branch of a primary or parent vessel, including one that has an acute reverse orientation. By controlling the proximal external hub portion of the catheter, the wing can be oriented to course along the desired wall of the catheterized vessel until the orifice of the branching vessel is located, thereby permitting the catheter to be further advanced into the branching vessel. The catheter of this invention permits rapid and safe catheterization of cerebral vessels without the use of a guidewire and without tip stem curvature. Multiple embolic agents can be used with the catheter and it is particularly well suited for the use of liquid adhesives. It can be employed in highflow vessels, and the microcatheter is also functional in cerebral vessels of normal flow.

The size of the wing-shaped. guide structure is operational on the scale commonly encountered in cerebral microcatheters. It has particular applicability in the treatment of cerebral arterial venous malformations, especially using liquid adhesives.

Thus, the present invention provides a catheter device for therapeutic and diagnostic use within a human vascular system. The catheter has a cylindrical catheter body formed around a lumen, with a hub located at a proximal end of the catheter body, and a tip located at a distal end of the body. A guide structure is connected to the catheter body proximate the tip, with the guide structure having a wing shape that provides hemodynamic lift in response to laminar blood flow around the catheter. The wing shape of the guide structure tapers down from a leading edge to a trailing edge, with the leading edge facing the catheter tip so that when the catheter is positioned inside a vessel wall of the vascular system and oriented in a downstream direction, the lift created by the laminar blood flow biases the catheter tip toward the vessel wall. Preferably, the distal end of the catheter body comprises a flexible material so that the catheter tip can deflect and move towards the vessel wall in response to the hemodynamic lift. An intermediate section of the catheter body between the hub and the tip provides a semi-rigid control connection whereby pushing, pulling, and rotation of the hub produces a corresponding movement of the catheter tip.

DESCRIPTION OF THE PREFERRED EMBODIMENTS

Figure 1A:
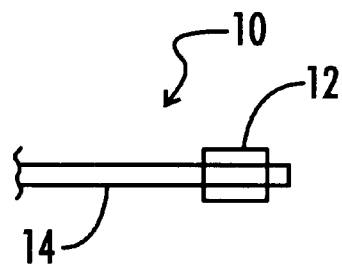
FIG. 1A is a side view of the catheter of the present invention shown in schematic form to demonstrate the size of the guide structure relative to the catheter body.
Figure 1B:
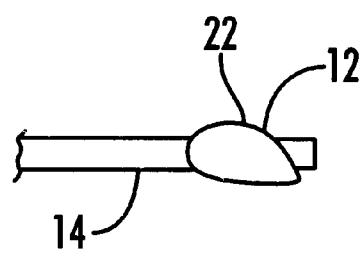
FIG. 1B is a side view of the catheter of the present invention showing the wing shaped profile of the guide structure.
Figure 2:
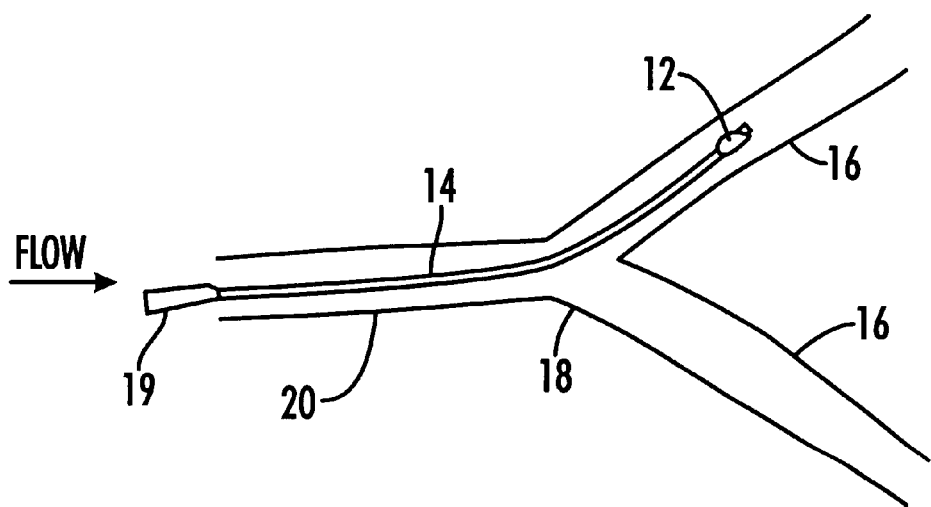
FIG. 2 is a cutaway side view of a portion of a bifurcated vessel system with the catheter of the present invention positioned within the wall of a branch vessel.
Figure 3:
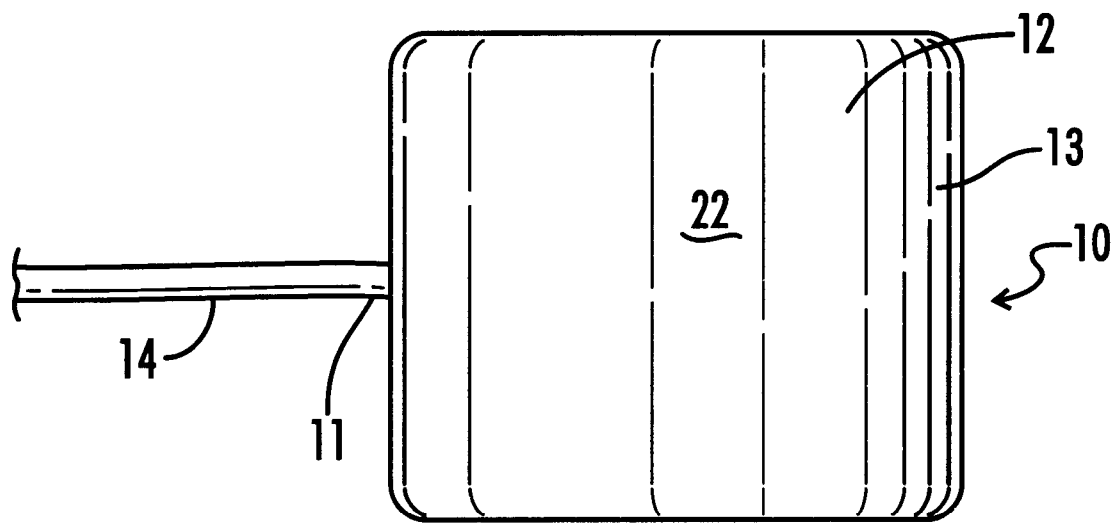
FIG. 3 is an enlarged plan view of the distal end of the catheter, showing the guide structure attached to the catheter tip.
Figure 4:
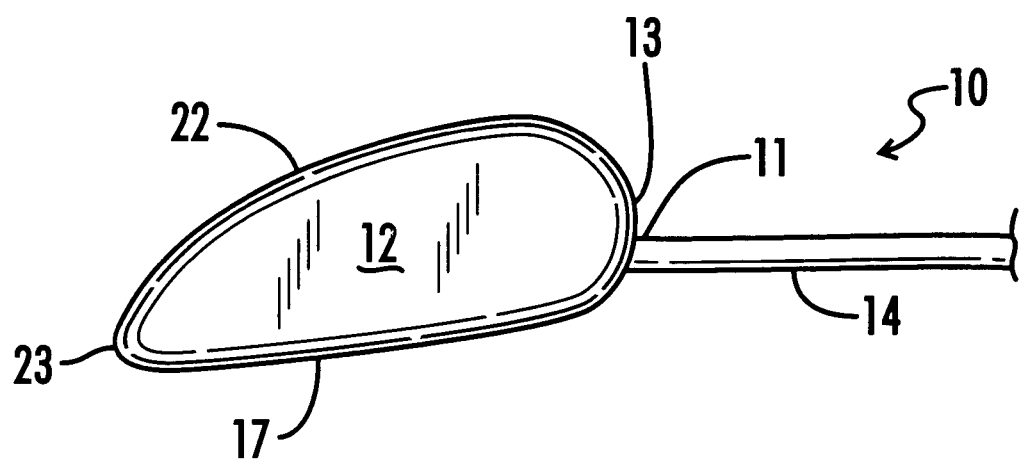
FIG. 4 is an enlarged side view of the distal end of the catheter, showing the guide structure attached to the catheter tip.

Looking first at FIGS. 1A through 4, the present invention is directed towards a catheter 10 with an auxiliary guide structure 12 attached to the catheter tip 11 at the distal end of a catheter body 14. The catheter body is conventional in design, having a cylindrical wall formed around a lumen. A conventional hub 19 is located at the proximal end of the catheter body 14 (FIG. 2) to aid in manipulation of the catheter tip 11, including movement downstream, upstream, and rotation. As best seen in FIG. 4, the guide structure 12 is provided with a wing-shape that uses the Bernoulli effect to create hemodynamic. lift from laminar blood flow through the vessel 20. This allows the guide to be used to steer the catheter 10 through vessels 20 and into specific branches 16 of vessel bifurcations 18 (FIG. 2). In accordance with a preferred embodiment, the guide structure 12 (FIG. 4) has a convex leading edge 13 proximate to catheter tip 11 that tapers inward toward a trailing edge 23, a convex curved top surface 22, and a substantially planar bottom surface 17. Those familiar with fluid dynamics, and the Bernoulli effect in particular, will recognize that the wing shape combined with a proper angle of attack within a laminar blood flow will produce a lifting force that will bias the catheter tip 11 toward the vessel wall. If, as in the preferred embodiment, the tip 11 of the catheter body 14 is flexible, the tip 11 will deflect laterally toward the vessel wall in the presence of laminar blood flow. The guide structure 12 can be manufactured so that it is formed integral to the tip 11 or bonded to the tip using a bio-resistant and bio-inert adhesive.

Figure 5A:
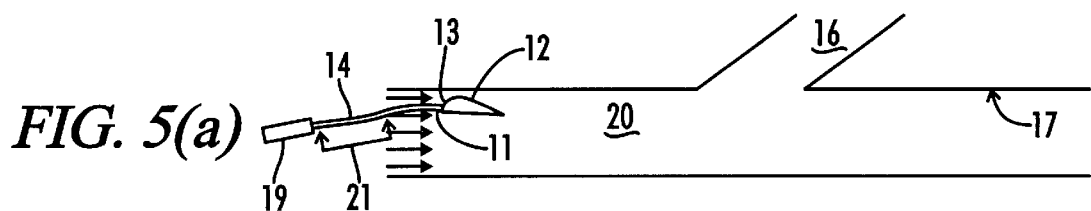
FIGS. 5(a)–(c) are a sequence of schematic drawings showing the distal end of the catheter of the present invention as it moves through a primary vessel.
Figure 5B:
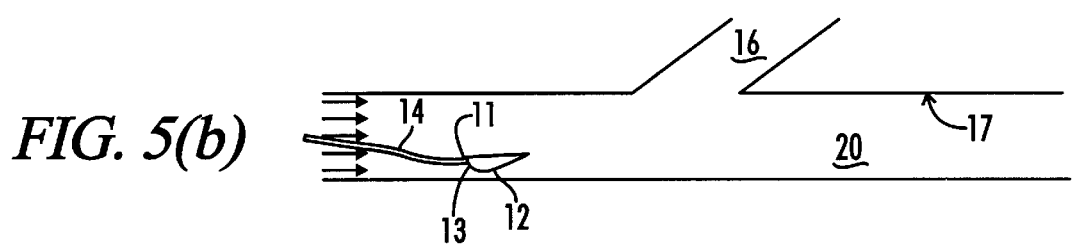
Figure 5C:
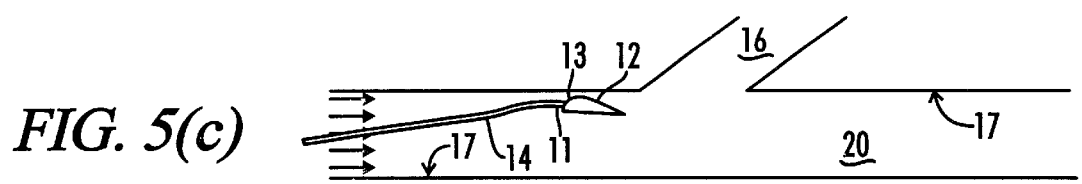
Figure 5D:
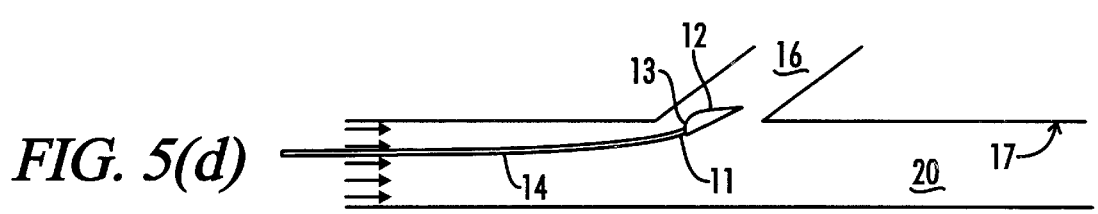
FIGS. 5(d)–(e) show the catheter of FIGS. 5(a)–(c) being moved into a branch vessel using hemodynamic lift produced by the wing-shaped guide structure.
Figure 5E:
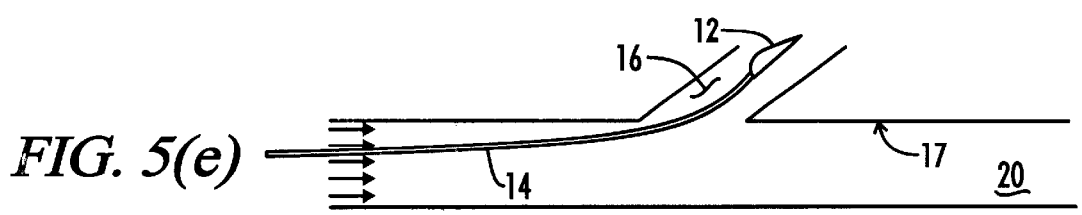

FIGS. 5(a) through 5(e) illustrate the movement of the catheter 10 through a primary vessel 20 towards a branch vessel 16. The leading edge 13 of the guide structure 12 is oriented upstream, that is, opposite the direction of blood flow. The trailing edge 23 is opposite the leading edge. Accordingly, the lift generated in the guide structure 12 causes the tip 11 of the catheter 10 to "hug" the wall 17 of the vessel 20. In FIGS. 5(d) and 5(e), the lift causes the catheter tip 11 and distal portion of the body 14 to move into the branch vessel 16. Preferably, the section 21 of the catheter body 14 that is intermediate the catheter hub 19 and tip 11 (FIGS. 2 and 5(a)) is made of a material that is axially flexible so that the catheter body 14 can curve through turns in the vasculature. The intermediate section 21 must also have sufficient rigidity so that manipulation from the insertion point, including rotation, of the hub 19 will cause a corresponding movement of the tip 11. Conventional catheter materials, such as polyethylene, can be used in the manufacture of the catheter body 14.

Figure 6:
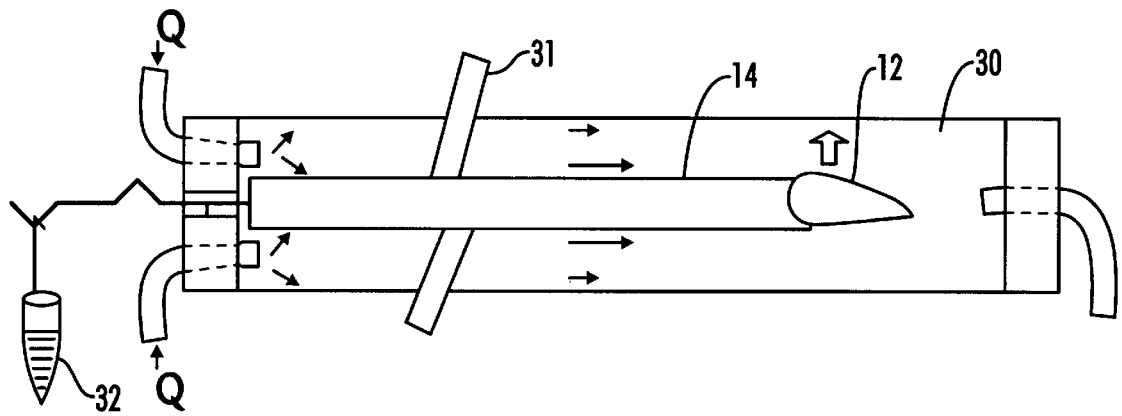
FIG. 6 is a schematic diagram of a test apparatus that can be used to determine the proper size, shape, and attack angle of the catheter guide structure for use in a particular application in accordance with the present invention.

The precise size and shape of the guide structure 12 will depend, of course, on the application for which the catheter 10 is to be used, including. the size of the primary and branch vessels and the rate of blood flow. A design and test apparatus can be used to determine an optimum size, shape, and angle of attack for a particular application. Thus, the lift force generated by different guide structure 12 configurations can be measured using a 10× scale dynamic similarity model that matches Reynold's numbers with those of in vivo flow conditions. An example of such a test apparatus is shown in FIG. 6. The catheter body 14 is suspended 31 within a test vessel 30. Fluid having viscous properties similar to blood is injected at points Q to produce a laminar flow through the test vessel 30. A counterbalance weight 32 is varied until a balanced state is achieved within the flowing fluid. The corresponding lift force necessary to displace the catheter 14 inside a real vessel 20 under similar flow conditions can then be determined. Subsequent 3× scale and actual size dynamic similarity models confirmed that a wing-shaped guide structure 12 can be used to steer the catheter body 14 into specific branches 16 of bifurcations 18 under in vivo flow conditions.

Figure 7:
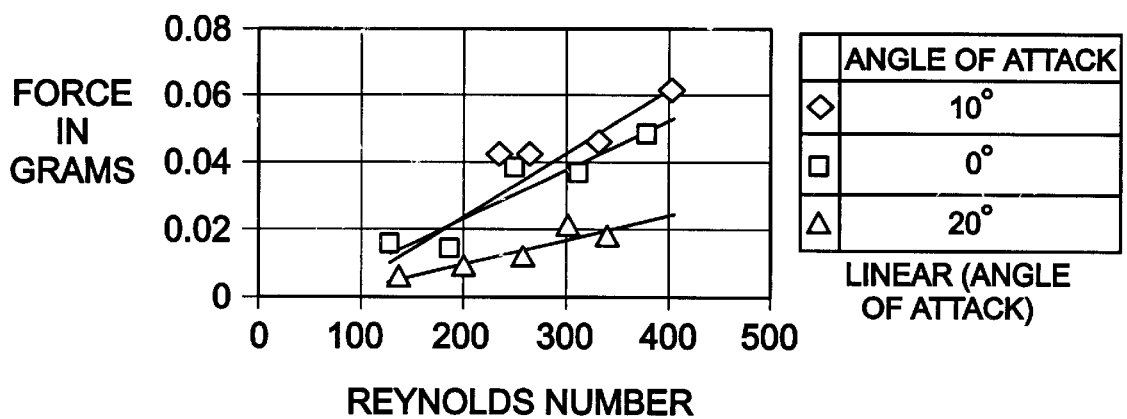
FIG. 7 is a graphical representation of the relationship between lift force produced by a guide structure in accordance with the present invention as a function of Reynolds Number, at different angles of attack.

FIG. 7 graphically illustrates lift force as a function of Reynold's Number and angle of attack. Hemodynamic Reynold's Numbers in the human cervical and cerebral vasculature range from 350 to 750 under normal circumstances corresponding to flow velocities of 20–50 cm/sec. In a typical major cerebral artery, blood flow velocities range from 20 cm/sec (Reynolds No. =350) to 127 cm/sec. (Reynolds No. =1450). For example, an internal carotid artery in a human may have an inside diameter of 0.457 cm, a flow velocity of 21 cm/sec, and a Reynolds Number of 355. These Reynold's Numbers indicate that a wing-shaped guide structure 12 will produce directional movement of the tip 11. This application of the Bernoulli effect neglects blood's viscous forces. However in human vascularity, inertial force is dominant, making a good approximation of Bernoulli's equation reasonable. Therefore, this causes the guide structure 12 and distal catheter tip 11 to lift and hug the vessel wall 17. Precise calculation of the angle of attack optimizes lift and drag forces, preventing boundary layer separation.

Laminar blood flow is necessary for optimal lift while turbulent flow reduces lift. Vessel 20 geometry such as widening at bifurcations 18, degree of bifurcation angle, tapering, curvation, intimal surface irregularity, vessel wall elasticity, and pulsatile flow can increase or decrease corresponding Reynold's Numbers and the subsequent effectiveness of the microcatheter 10. For example, boundary layer separation at vessel bifurcation 18 produces turbulent flow. This disrupted flow pattern typically is located along the proximal side of a branching vessel orifice, opposite to the wall of the vessel wall where the microcatheter would navigate. Furthermore, the vascular flow zone of influence in the primary vessel's termination would carry the microcatheter 10 into the selected branching vessel.

One embodiment of an optimal microcatheter 10 would have an intermediate degree of stiffness, enough to push, pull, or rotate the catheter body 14 including the tip 11 and guide structure 12, yet permit tip deflection by the guide structure 12. In addition, high flow intracranial lesions for which this catheter 10 is intended would further increase Reynold's Number and make the wing structure 14 more efficient by increasing the blood velocity over the structure 12 and therefore its consequent lift. The fact that the guide structure 12 does not obstruct the distal tip 11 permits usage of conventional microguidewires. This design also allows for the delivery of any number of embolic agents, especially liquid adhesives. By providing lift to the catheter tip 11, once this enters the orifice or immediately proximal segment of a desired vessel 20, the remainder of the vessel 20 can be catheterized by simply pushing the microcatheter 10. Catheter directionality is achieved by rotating the external, proximal catheter hub 19, causing a rotation of the guide structure 12 and a corresponding change in direction of the lift forces.

For a catheter 10 that would be usable in human cervical and cerebral vessels, a guide structure 12 having a 1 mm diameter catheter body 14 (3 French) and guide structure that is 1 mm tall, 2 mm wide, and 2 mm long, provides sufficient directional lift.

The microcatheter 10 of this invention permits directional control of its tip 11 to enable catheterization of branch vessels 16 without the use of a guidewire. A guidewire may be used, however, as may a multitude of embolic agents. Because the present invention takes advantage of hemodynamic flow, the target lesions intracranially can be reached faster and safer than currently available in commercial products.

Thus, although there have been described particular embodiments of the present invention of a new and useful Microcatheter with Hemodynamic Guide Structure, it is not intended that such references be construed as limitations upon the scope of this invention except as set forth in the following claims.

What is claimed is:

1. A catheter device for therapeutic and diagnostic use within a human vascular system comprising:
   a. a catheter body, a hub located at a proximal end of the body, and a tip located at a distal end of the body; and
   b. a guide structure connected to the catheter body proximate the tip, the guide structure having a wing shape that provides hemodynamic lift in response to laminar blood flow around the catheter.

2. The device of claim 1 wherein the wing shape of the guide structure tapers down from a leading edge to a trailing edge, with the leading edge facing the catheter tip so that when the catheter is positioned inside a vessel wall of the vascular system and oriented in a downstream direction, the lift created by the laminar blood flow biases the catheter tip toward the vessel wall.

3. The device of claim 2 wherein the distal end of the catheter body comprises a flexible material so that the catheter tip can deflect and move towards the vessel wall in response to the hemodynamic lift.

4. The device of claim 3 wherein an intermediate section of the catheter body between the hub and the tip provides a semi-rigid control connection whereby pushing, pulling, and rotation of the hub produces a corresponding movement of the catheter tip.

5. The device of claim 4 wherein the guide structure is rigidly attached to the tip so that rotation of the hub produces a corresponding re-orientation of the guide structure within the vessel wall.

6. The device of claim 5 wherein the wing shape comprises a convex leading edge, a convex upper surface, and a substantially planar lower surface.

7. A method of guiding a catheter device through a portion of a human vascular system comprising:
   a. introducing the catheter into a primary vessel of the vascular system, the catheter having a guide structure attached near a flexible tip of the catheter, the guide structure formed into a wing shape adapted to produce hemodynamic lift in response to laminar blood flow around the guide structure;
   b. orienting the catheter tip in the direction of laminar blood flow through the primary vessel, with a leading edge of the guide structure shape directed upstream; and
   c. rotating the catheter tip to cause a re-orientation of the guide structure within the laminar blood flow so that the corresponding lift produced by the guide structure moves the catheter tip in a desired direction.

8. The method of claim 7 further comprising moving the catheter tip downstream through the primary vessel towards an opening into a branch vessel, and rotating the catheter tip so that the lift produced by the guide structure moves the catheter tip into the branch vessel.

9. A guided catheter comprising a flexible catheter body terminating at a flexible catheter tip and a hemodynamic wing attached to the catheter tip, the wing shaped and oriented to flex the catheter tip laterally in response to laminar blood flow across the wing.

* * * * *